(12) United States Patent
Zhang

(10) Patent No.: US 9,063,134 B2
(45) Date of Patent: Jun. 23, 2015

(54) MULTI-UNIT PLATE FOR IMMUNOBLOT ANALYSIS

(71) Applicant: Jiandi Zhang, Fairfax, VA (US)

(72) Inventor: Jiandi Zhang, Fairfax, VA (US)

(73) Assignee: Yantai Zestern Biotechnique Co. LTD, Bioasis, Yantai Hi-tech Distric, Yantai (CN)

( * ) Notice: Subject to any disclaimer, the term of this patent is extended or adjusted under 35 U.S.C. 154(b) by 0 days.

(21) Appl. No.: 13/936,890

(22) Filed: Jul. 8, 2013

(65) Prior Publication Data

US 2015/0011437 A1 Jan. 8, 2015

Related U.S. Application Data

(60) Provisional application No. 61/669,650, filed on Jul. 9, 2012.

(51) Int. Cl.
*G01N 33/543* (2006.01)

(52) U.S. Cl.
CPC .... *G01N 33/54366* (2013.01); *G01N 33/54353* (2013.01)

(58) Field of Classification Search
CPC ............ B01L 9/523; B01L 2300/0893; B01L 3/5085; B01L 3/50853
USPC .................................................. 422/553, 942
See application file for complete search history.

(56) References Cited

U.S. PATENT DOCUMENTS

| | | | | |
|---|---|---|---|---|
| 5,496,737 A * | 3/1996 | Bickar | ............................. | 436/86 |
| 5,679,310 A * | 10/1997 | Manns | ............................ | 422/553 |
| 5,731,161 A * | 3/1998 | Aoki et al. | ................... | 435/7.32 |
| 8,293,487 B1 | 10/2012 | Zhang | | |
| 2007/0218546 A1* | 9/2007 | Steuer et al. | ................ | 435/287.2 |
| 2010/0190197 A1* | 7/2010 | Martin et al. | .................... | 435/29 |

* cited by examiner

*Primary Examiner* — Jill Warden
*Assistant Examiner* — Matthew Krcha

(57) ABSTRACT

This invention provides for multi-unit plates that comprise a layer of membrane, preferably nitrocellulose or PVDF membrane, on the surface of individual unit of the multi-unit plate. These multi-unit plates are particularly well suited for high throughput immunoblot analysis including Zestern analysis.

9 Claims, 2 Drawing Sheets

US 9,063,134 B2

MULTI-UNIT PLATE FOR IMMUNOBLOT ANALYSIS

RELATED APPLICATIONS

This application claims the benefit of provisional application 61/669,650 filed on Jul. 9, 2012.

FIELD OF INVENTION

The present invention relates to the field of immunoassay and more particularly, to devices and method for Zestern analysis. Specifically, the present invention is of improved multi-unit plates and methods for performing Zestern analysis in a multi-unit format.

BACKGROUND ART

Protein analysis is the foundation of modern biological research. Investigations of the expression and regulation of critical protein factors in biological processes and their applications in pharmaceutical and clinical studies provide vital information for experimental, pharmaceutical and clinical research of the pathogenesis of diseases and their prevention, diagnosis and treatments.

The recently patented Zestern technique (U.S. Pat. No. 8,293,487) is an improvement of traditional methods of immunoblot-based protein analysis. While the protein samples are analyzed following a traditional immunoblotting process before detection, an additional step of elution is added in Zestern analysis to ensure the specificity of the assay. The antibody or antibody complex bound to the antigen of interest can be specifically competed out by competing molecule into elution solution. The amount of the eluted antibody or antibody complex in elution solution reflects reliably the amount of antigen of interest in the sample to be analyzed. The total amount of eluted antibody or antibody complex can be quantified directly in solution, representing another advantage of Zestern analysis over traditional immunoblotting methods.

While Zestern analysis demonstrates clear advantage over traditional immunoblot methods for its simplicity and suitability for high throughput analysis, it poses new demand for suitable devices, as current existing devices for traditional immunoblot methods are not designed to meet the need of Zestern analysis, especially for the high throughput purpose.

In traditional immunoblot analysis, represented by Western blot analysis, several types of membranes have been used, and have been well optimized for immunoblot analysis. These membranes include both nitrocellulose membrane and PVDF membrane. Nonetheless, in traditional immunoblot analysis, the signal is detected on the very spot where the antibody or antibody complex bound to the antigen of interest on the membrane. This requires the membrane to be flat and continuous to facilitate comparison of the detection results.

On the contrary, in Zestern analysis, antibody or antibody complex is liberated from the very spot where antibody or antibody complex bound to the antigen of interest by the competing molecule. The antibody or antibody complex is eluted individually from each spot for quantification. Clearly, in Zestern blot analysis, the membrane cannot be continuous among protein samples. It must be separate from each other to allow elution of antibody or antibody complex from individual protein sample, preventing cross-contamination of the signals from each other.

In Zestern analysis, for the membrane per se, there is no requirement regarding the shape or other physical characteristics of the membrane used, as detection of the signal from each sample is not being processed on the membrane.

A multi-well plate, has been widely used in biochemical assays and immunoblotting assays including ELISA assay. These multi-well plates include 6, 24, 96, and even 1536 well plate. It can also be referred as microtiter plate, microplate, or microwell plate.

Multi-well plate for ELISA assay generally has protein binding affinity at less than 1 $\mu g/cm^2$. In contrast, a typical membrane for traditional immunoblotting, regardless of nitrocellulose or PVDF membrane, has protein binding affinity of 100 to 200 $\mu g/cm^2$. While ELISA plate has achieved success in ELISA assay, its low protein binding capacity limits its application in Zestern analysis.

Therefore, this invention provides solution to the unique demand of Zestern analysis for immunoblot analysis, especially for its application in multi-unit plate format.

SUMMARY OF THE INVENTION

The present invention provides method and device and a variation of this method with matching device for high throughput immunoblot analysis including Zestern analysis. While the devices for each method are different from each other, they share the common feature of individual membrane unit on the surface of individual unit of multi-unit plate.

In Zestern analysis, membrane used for individual sample is referred as individual membrane unit. An individual membrane unit is a piece of membrane, or pieces of membrane together in each unit of the multi-unit plate, used for individual sample application. The individual membrane unit is separate from other individual membrane unit. The individual membrane unit is eluted in the elution step for quantification of the individual sample.

There is no limitation of the shape, texture or even the continuation of the membrane for individual membrane unit. Multiple pieces of membrane can be considered as one individual membrane unit as long as they are within one unit of multi-unit plate.

One method of Zestern analysis is to use modified multi-well plate. A modified multi-well plate wherein at the bottom surface of at least one well of the plurality of wells is one individual membrane unit, preferably either PVDF or nitrocellulose membrane. Preferably, a plate of the present invention has a footprint of a standard multiwall plate. Preferably, the plurality of wells of a plate of the present invention comprises 6n wells arranged in a 2n by 3n array, where n is an integer greater than 0, the wells preferably being arranged in rectangular packing. Preferred pluralities of wells are the commonly known pluralities of well such as 6, 24, 96, 384 and 1536 wells. More preferred are plates of 96 wells and 384 wells as these formats are most popular and have many available accessories including fluid handling accessories such as fluid-handling robots.

In one embodiment of the present invention, the individual well in multi-well plate can be individually addressable.

A multi-well plate of the present invention is made of any suitable material. Suitable materials include but are not limited to ceramics, elastomers, epoxies, glasses, glass-ceramics, metals, plastics, polycarbonates, polydimethlsiloxane, polyurethane, polyethylenterephatalate glycol, polymers, polymethyl methacrylate, polystyrene, polyvinyl chloride, rubber, silicon, silicon oxide and silicon rubber.

In an embodiment of the present invention, the bottom surface of the wells is made of any suitable material with protein binding affinity comparable to nitrocellulose or PVDF membrane. The entire plate of the present invention can be made of one material, or it can be made of a number of different materials, for example, a plurality of layers or as a coated structure.

The wall of individual well of the multi-well plate serves as physical barrier to prevent cross contamination of elution solution from each other. The bottom of the individual well of the multi-well plate prevents leaking of elution solution to affect the accuracy of the measurement.

In an embodiment of the present invention, the bottom of individual well in the multi-well plate is covered with individual membrane unit with flat surface. In another embodiment of the present invention, the surface of individual membrane unit covering the bottom of the individual well of multi-well plate may not be flat.

In an embodiment of the present invention, there is no limitation of the shape or 3-dimision-structure of the individual membrane unit covering the bottom of the multi-well plate as long as it allows accessibility of the samples of interest. In yet another embodiment, the membrane covering the bottom of the individual well may extend to the wall of individual well.

In an embodiment of the present invention, the individual membrane unit may not cover the bottom of the multi-well plate. It may associated with either the wall of individual well, or the bottom of individual well in a multi-well plate.

In an embodiment of the present invention, the individual membrane unit may be treated before or after sample application to increase protein binding efficiency.

A variation of the present invention for Zestern analysis is to use a multi-unit device in combination with a typical multi-well plate. The multi-unit plate is a plate with multi-protrusions where at least at the surface of at least one protrusion of the plurality of the protrusions is individual membrane unit, preferably either PVDF or nitrocellulose membrane. Preferably, a plate of the present invention has a footprint of a standard multiwall plate. Preferably, the plurality of protrusions of a plate of the present invention comprises 6n protrusions arranged in a 2n by 3n array, where n is an integer greater than 0, the protrusions preferably being arranged in rectangular packing. Preferred pluralities of protrusions are the commonly known pluralities of protrusions such as 6, 24, 96, 384 and 1536 protrusions. More preferred are plates of 96 protrusions and 384 protrusions as these formats are most popular and have many available accessories including fluid handling accessories such as fluid-handling robots.

The multi-unit plate has at least one protrusion which is separated from other protrusion of the plurality of the protrusions in multi-unit plate.

The present invention of multi-unit plate of protrusions can fit smoothly into a typical multi-well plate with matching number of protrusions and wells for Zestern analysis.

In one embodiment of the present invention, the individual protrusion in multi-unit plate can be individually addressable.

A multi-unit plate of the present invention is made of any suitable material. Suitable materials include but are not limited to ceramics, elastomers, epoxies, glasses, glass-ceramics, metals, plastics, polycarbonates, polydimethylsiloxane, polyurethane, polyethylenterephatalate glycol, polymers, polymethyl methacrylate, polystyrene, polyvinyl chloride, rubber, silicon, silicon oxide and silicon rubber.

In an embodiment of the present invention, the surface of the protrusion is made of any suitable material with protein binding affinity comparable to nitrocellulose or PVDF membrane. The entire plate of the present invention can be made of one material, or it can be made of a number of different materials, for example, a plurality of layers or as a coated structure.

In an embodiment of the present invention, the surface of individual protrusion in the multi-unit plate is completely covered with individual membrane unit with flat surface. In another embodiment of the present invention, the surface of individual membrane unit covering the surface of the individual protrusion of multi-unit plate may not be flat.

In an embodiment of the present invention, there is no limitation of the shape or 3-dimision-structure of the individual membrane unit covering the surface of the individual protrusion of multi-unit plate as long as it allows accessibility of the samples of interest.

In an embodiment of the present invention, the individual membrane unit of the individual protrusion from multi-unit plate maybe treated before or after sample application to increase protein binding efficiency.

DETAILED DESCRIPTION OF THE INVENTION

Unless defined otherwise, all technical and scientific terms used herein have the same meaning as is commonly understood by one of skills in the art to which this invention belongs.

The present invention provides devices for Zestern analysis. Zestern analysis distinguishes itself from traditional blot analysis including Western blot analysis by its simplicity and suitability for multi-unit format. The elution step in Zestern analysis also requires elution solution for individual sample to be physically separated from each other to avoid cross-contamination of the results. In other word, each sample must be applied to individual membrane unit, and elution solution for individual sample must be limited to individual membrane unit.

Figure 1:
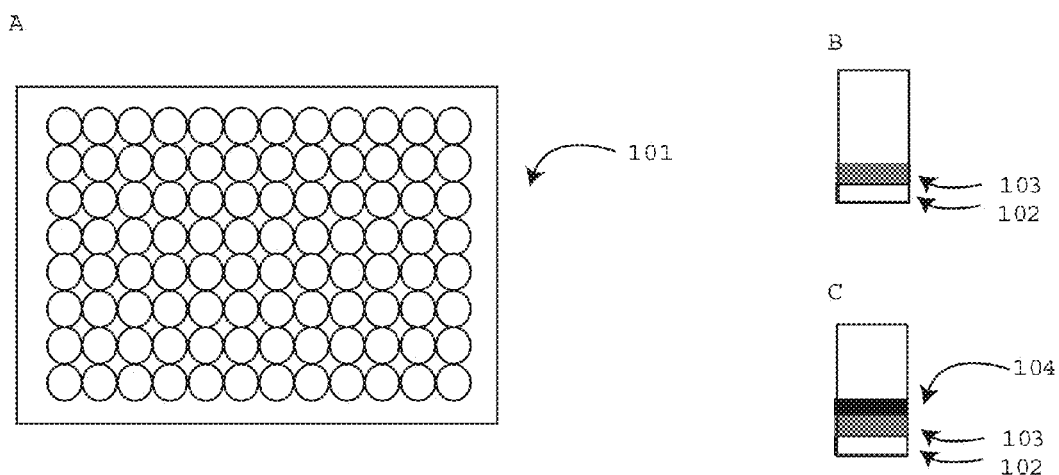
FIG. 1 shows an embodiment of multi-unit plate. 1A, top view of the modified multi-well plate; 1B, side view of the individual well of multi-well plate; 1C, side view of the individual well of multi-well plate when a sample is applied. 101, multi-unit plate of present invention; 102, bottom of the multi-well plate, 103, membrane covering the bottom of the individual well of multi-well plate.

In an embodiment of present invention, device for Zestern analysis is shown in FIG. 1. A modified multi-well plate 101 wherein at the bottom surface of at least one well of the plurality of wells is one individual membrane unit 103 on top of the bottom of the individual well 102. Sample to be analyzed 104 is to be applied directly on the individual membrane unit 103. Individual membrane unit 103 is preferably either PVDF or nitrocellulose membrane. Preferably, a plate of the present invention has a footprint of a standard multiwall plate. Preferably, the plurality of wells of a plate of the present invention comprises 6n wells arranged in a 2n by 3n array, where n is an integer greater than 0, the wells preferably being arranged in rectangular packing. Preferred pluralities of wells are the commonly known pluralities of well such as 6, 24, 96, 384 and 1536 wells. More preferred are plates of 96 wells and 384 wells as these formats are most popular and have many available accessories including fluid handling accessories such as fluid-handling robots.

The surface of the individual membrane unit can be flat, or it can be coarse. It can also have protrusions on the surface of the individual membrane unit. The individual membrane unit may covers the bottom of the well of multi-well plate, or it may extend to the wall of individual well of multi-well plate as long as individual membrane unit is separated from each other within multi-well plate.

Figure 2:
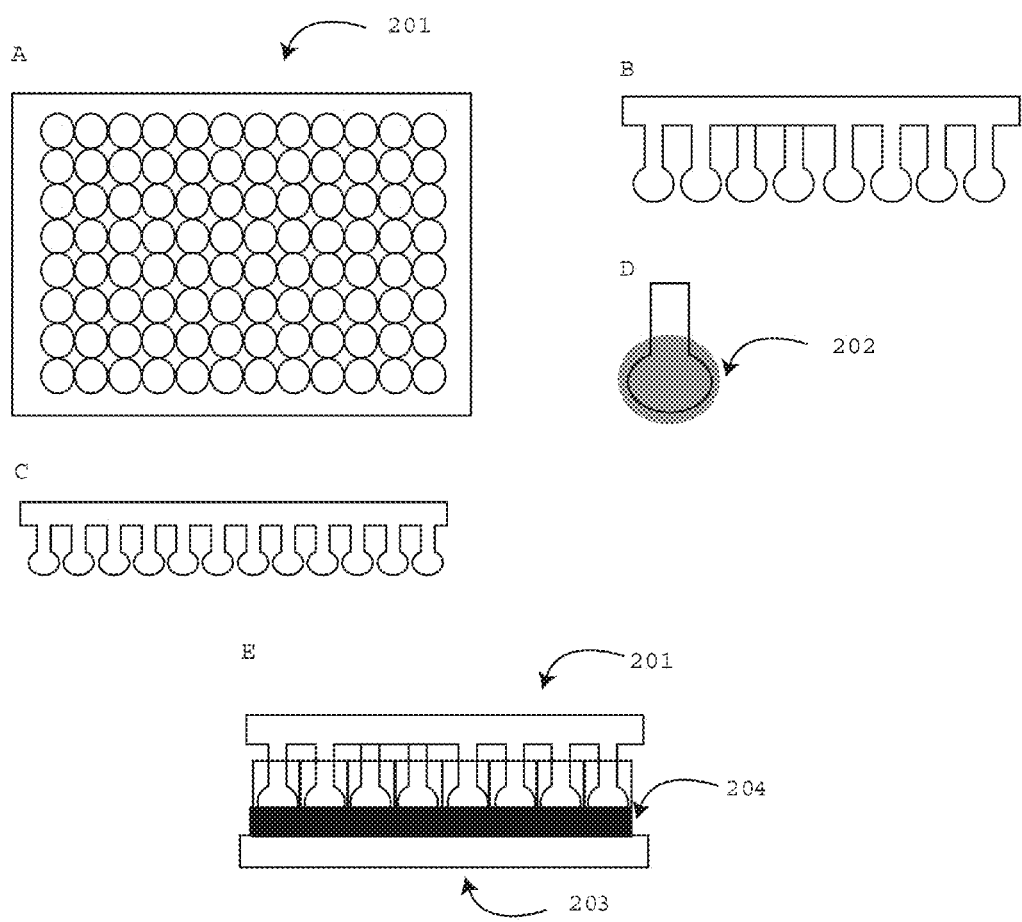
FIG. 2. Shows another embodiment of multi-unit plate. 2A, top view of the modified multi-unit plate. 2B, vertical side view of multi-unit plate; 2C, horizontal side view of the multi-unit plate. 2D, side view of individual unit of multi-unit plate; 2E, the insertion of multi-unit plate into multi-well plate during sample application and elution steps. 201, multi-unit plate of present invention; 202, the membrane coating the protrusion from multi-unit plate. 203, regular multi-well plate; 204, samples to be analyzed in the individual well of multi-well plate.

An variation of embodiment 101 is shown in FIG. 2. A multi-unit-plate 201 is a plate with multiple protrusions on the surface of the plate. This device is in combination with a typical multi-well plate for Zestern analysis. The multi-unit plate is a plate with multi-protrusions where at least at the surface of at least one protrusion of the plurality of the protrusions is individual membrane unit, preferably either PVDF or nitrocellulose membrane.

Preferably, a plate of the present invention has a footprint of a standard multiwall plate. So, the multi-unit plate can fit inside a typical multi-well plate as shown in FIG. 2E. Preferably, the plurality of protrusions of a plate of the present invention comprises 6n protrusions arranged in a 2n by 3n array, where n is an integer greater than 0, the protrusions preferably being arranged in rectangular packing. Preferred pluralities of protrusions are the commonly known pluralities of protrusions such as 6, 24, 96, 384 and 1536 protrusions. More preferred are plates of 96 protrusions and 384 protrusions as these formats are most popular to find matching multi-well plate, and have many available accessories including fluid handling accessories such as fluid-handling robots.

The individual protrusion 202 of multi-unit plate 201 is completely covered on the surface with individual membrane unit. The multi-unit plate 201 of the present invention is made of any suitable material. Suitable materials include but are not limited to ceramics, elastomers, epoxies, glasses, glass-ceramics, metals, plastics, polycarbonates, polydimethylsiloxane, polyurethane, polyethylenterephatalate glycol, polymers, polymethyl methacrylate, polystyrene, polyvinyl chloride, rubber, silicon, silicon oxide and silicon rubber.

In an embodiment of current invention, multi-unit plate 201 can be inserted into a typical multi-well plate 203 containing samples 204 in individual well of multi-well plate as shown in FIG. 2E. Multi-unit plate 201 can be left in the air to dry, and the multi-protrusions of multi-unit plate are inserted into appropriate containers to go through a typical immunoblot process including steps of blocking, primary antibody incubation, washing, secondary incubation and wash again.

The multi-unit plate 201 with immunocomplex bound on the individual membrane unit of the protrusions of the plate is inserted into a typical multi-well plate 202 after a typical immunoblotting process. Elution solution containing appropriate competing molecule is used in each well of multi-well plate 203 to elute antibody or antibody complex from the individual membrane unit on the surface of the protrusion of the multi-unit plate 201 for quantification of the signals.

In an embodiment of the present invention, the surface of the protrusion is made of any suitable material with protein binding affinity comparable to nitrocellulose or PVDF membrane. The entire plate of the present invention can be made of one material, or it can be made of a number of different materials, for example, a plurality of layers or as a coated structure.

As used herein "membrane" is to be taken in its broadest context. A membrane can be any material within sufficient surface porosity to allow access by detection antibodies and a suitable surface affinity to bind antigen. All these materials may be used in suitable shapes, or they can be coated onto, or bonded or laminated, or simply attached to appropriate supporting materials, such as paper, glass, plastic materials. For example, membrane can be, but not limited to, nitrocellulose membrane or PVDF membrane.

Those skilled in the art will know how to prepare samples for immunoblot purpose. The samples include, but not limited to, a mixture of a chemical molecule, a peptide molecule, a protein molecule, an RNA molecule, a DNA molecule, a traditional antibody, e.g., two heavy chains and two light chains, a recombinant antibody or fragment, a bacteria cell, a virus particle, and a product comprising crosslinking any two or more of the above. The sample may be charged with appropriate sample buffer.

Those skilled in the art will know how to treat membrane for immunoblot. These practices include, but not limited to, direct application of samples to the membrane, or pre-wet the membrane portion of the multi-well plate with Ethanol, or Methanol, before sample application. The multi-unit plate with sample applied on the membrane is left in the air to dry before going through a typical immunoblot process.

The membrane can also be treated before or after sample application to increase protein binding efficiency. This practice includes, but not limited to UV crosslinking, or applying electric current on the membrane loaded with sample to increase protein binding efficiency.

Those skilled in the art will know how to process individual membrane unit with samples applied on the surface for immunoblot process. These steps include blocking the individual membranes with blocking buffers, incubation with primary antibody, washing, incubation with secondary antibody and wash again to eliminate non-specific antibody binding to the individual membrane unit while preserving the immunocomplex bound on the surface of individual membrane unit.

In one embodiment of present invention, after the sample application step but before the elution step, multi-unit plate 201 can be processed in a container other than a multi-well plate 203.

It is appreciated that many alternatives, modifications and variations will be apparent to those skilled in the art. Accordingly, the present invention is intended to embrace all such alternatives, modifications and variations that fall within the spirit and broad scope of the appended claims.

The following examples of the method of invention are to further illustrate of the nature of the invention. It needs to be understood that the invention is not limited thereto.

Example 1

Samples of interest are prepared using 4×SDS buffer (Laemmli buffer). The 96 well plate of present invention with the bottom of individual well coated with nitrocellulose membrane will be loaded with samples of limited volume (20 µl per sample) to each well of 96 well plate. The 96-well plate loaded with prepared samples will be left in the air for 20 mins to allow the membrane to dry.

A typical immunoblot process, including steps of blocking, incubation with primary antibody, wash, incubation with secondary antibody, and wash, will be performed using this modified multi-well plate. The secondary antibody is labeled with Horseradish peroxidase as the reporter enzyme for immunoblot analysis.

For each individual well of this 96well plate, elution buffer containing competing molecule at appropriate volume (100 µl/well) will be added and incubated with the membrane for 30 mins to liberate antibody complex from the bottom of the individual well of multi-well plate.

The elution buffer will be transferred to a regular 96 well plate for quantification of the signaling using a typical chemiluminence reporter assay using a microplate reader.

Example 2

Samples of interests are prepared as described in example 1. These samples are loaded into a regular 96 well plate at volume of 20 μl.

Multi-unit plate with protrusions covered completely with individual membrane unit, arranged in the right order to ensure its insertion into 96 well plate, is inserted into 96 well plate containing samples of interest in individual well for 5 mins for sample application.

The multi-unit plate is removed from multi-well plate, and is left to dry for 20 mins before it is inserted into a large container containing 50 ml of blocking buffer and shake for 30 mins for blocking.

The multi-unit plate is incubated with primary antibody in blocking buffer at 50 ml in a large container and shake for another 2 hours before it is washed three times with TBST buffer, each time for 5 mins at volume of 50 mls in a large container.

The multi-unit plate is incubated with secondary antibody in blocking buffer at volume of 50 ml in a large container and shake for another 1 hour before it is washed again with TBST at 50 ml for three times, each time for 5 mins. The secondary antibody is labeled with Horseradish peroxidase as reporter enzyme.

While multi-unit plate being washed with TBST, a regular 96 plate containing appropriate competing molecule in individual well of the plate is prepared at the volume of 150 μl/well.

After wash, the multi-unit plate is inserted into 96 well plate containing elution solution in individual well of the plate and shake for 30 mins.

The multi-unit plate is removed from 96 well plate, and the elution solution from individual well of 96 well plate is used for quantification in a typical chemiluminesence assay using a microplate reader.

What I claimed:

1. A multi-unit device for immunodetection assay comprising:
    a multi-well plate with a plurality of wells; and
    a complementary multi-unit plate sized to fit into the multi-well plate; the multi-unit plate comprising a plurality of bulbous protrusions on a surface of the multi-unit plate, wherein the surface of the bulbous portion of all the protrusions are completely covered by a membrane.

2. The multi-unit plate of claim 1, wherein the membrane is treated before or after sample application to increase protein binding efficiency.

3. The multi-unit plate of claim 1, having a footprint of a standard multiwell plate to allow its insertion into a matching multi-well plate.

4. The multi-unit plate of claim 1, wherein said plurality of protrusions comprises 6n protrusions arranged in a 2n×3n array, where n is an integer greater than 0.

5. The multi-unit plate of claim 1, wherein said plurality of all protrusions comprises individually addressable protrusions.

6. The multi-unit plate of claim 1, wherein the membrane is sufficiently porous to allow penetration by the detection antibody.

7. The multi-unit plate of claim 1, wherein the membrane is nitrocellulose or PVDF membrane.

8. The multi-unit plate of claim 1, wherein the membrane is coarse.

9. The multi-unit plate and multi-well plate of claim 1, comprising a material selected from the group consisting of ceramics, elastomers, epoxies, glasses, glass-ceramics, metals, plastics, polycarbonates, polydimethylsiloxane, polyethylenterephatalate glycol, polymers, polymethyl methacrylate, polystyrene, polyurethane, polyvinyl chloride, rubber, silicon, silicon oxide and silicon rubber.

* * * * *